United States Patent [19]

Igarashi et al.

[11] 4,362,866
[45] Dec. 7, 1982

[54] APROSAMINE DERIVATIVES

[75] Inventors: Kikuo Igarashi, Itami; Tsunetoshi Honma, Ikoma, both of Japan

[73] Assignee: Shionogi & Co., Ltd., Osaka, Japan

[21] Appl. No.: 313,971

[22] Filed: Oct. 22, 1981

[30] Foreign Application Priority Data

Oct. 27, 1980 [JP] Japan ................... 55-150926

[51] Int. Cl.³ ............................. C07H 15/22
[52] U.S. Cl. ..................... 536/16.8; 424/180
[58] Field of Search ............ 536/17 R, 4; 424/118

[56] References Cited

U.S. PATENT DOCUMENTS 3,691,279  9/1972  Thompson et al. ............ 424/118
3,853,709 12/1974  Stark ........................... 424/118
3,876,767  4/1975  Ose ............................. 424/118

OTHER PUBLICATIONS

Abe et al., "The Jour. of Antibiotics", vol. XIV, 1981, pp. 1434–1443.
O'Connor et al., "Chem. Abst.", vol. 85, 1976, p. 21,760(t).

Primary Examiner—Johnnie R. Brown
Attorney, Agent, or Firm—Wenderoth, Lind & Ponack

[57] ABSTRACT

New aprosamine derivatives having the reinforced antimicrobial activity against gram-positive and negative bacteria with less side effects than apramycin, and produced by chemical modification of 8'-hydroxy group of aprosamine obtained by means of hydrolysis of apramycin.

2 Claims, No Drawings

APROSAMINE DERIVATIVES

BACKGROUND OF THE INVENTION

Chemical modifications of aminoglycoside antibiotics have been investigated intensively to enhance antimicrobial activity and reduce side effects. The inventors have found that chemical modification of the 8'-hydroxy group of aprosamine which is prepared by hydrolysis of Apramycin (for example, described as Nebramycin factor II in Jap. Exam. Pat. Pub. No. 51-36358) enhances the antimicrobial effect. The invention was completed on this result.

SUMMARY OF THE INVENTION

The present invention relates to new aprosamine derivatives having the following general formula (I).

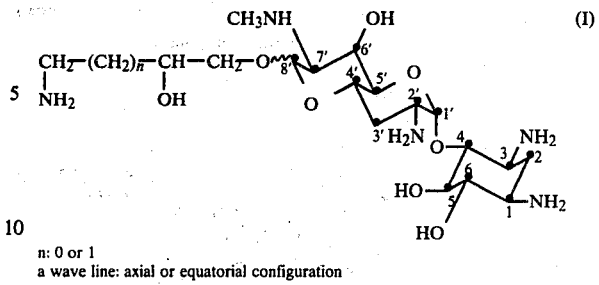

n: 0 or 1
a wave line: axial or equatorial configuration

In the present invention aprosamine derivatives having the formula (I) include also the free base and its salts, particularly pharmaceutically acceptable non-toxic acid addition salts. As acids which can form the salts, for example, inorganic acids (hydrochloric acid, hydrobromic acid, hydroiodic acid, sulfuric acid, phosphoric acid, carbonic acid, etc.) and organic acids (acetic acid, fumaric acid, malic acid, tartaric acid, maleic acid, citric acid, mandelic acid, ascorbic acid, gallic acid, etc.) are mentioned.

The compounds (I) in the present invention are produced accordingly to the following reaction sequence.

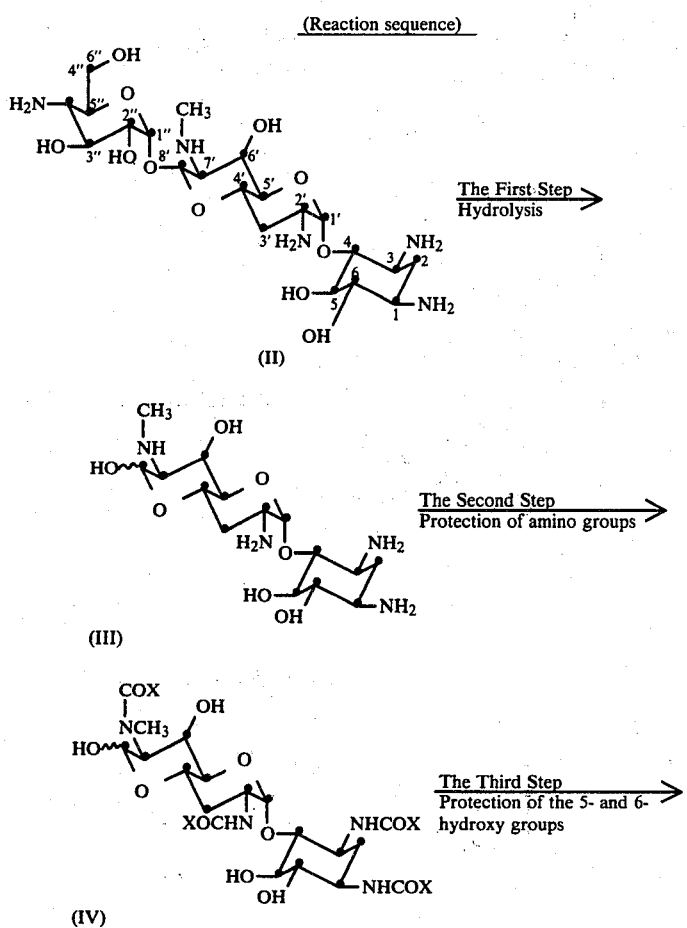

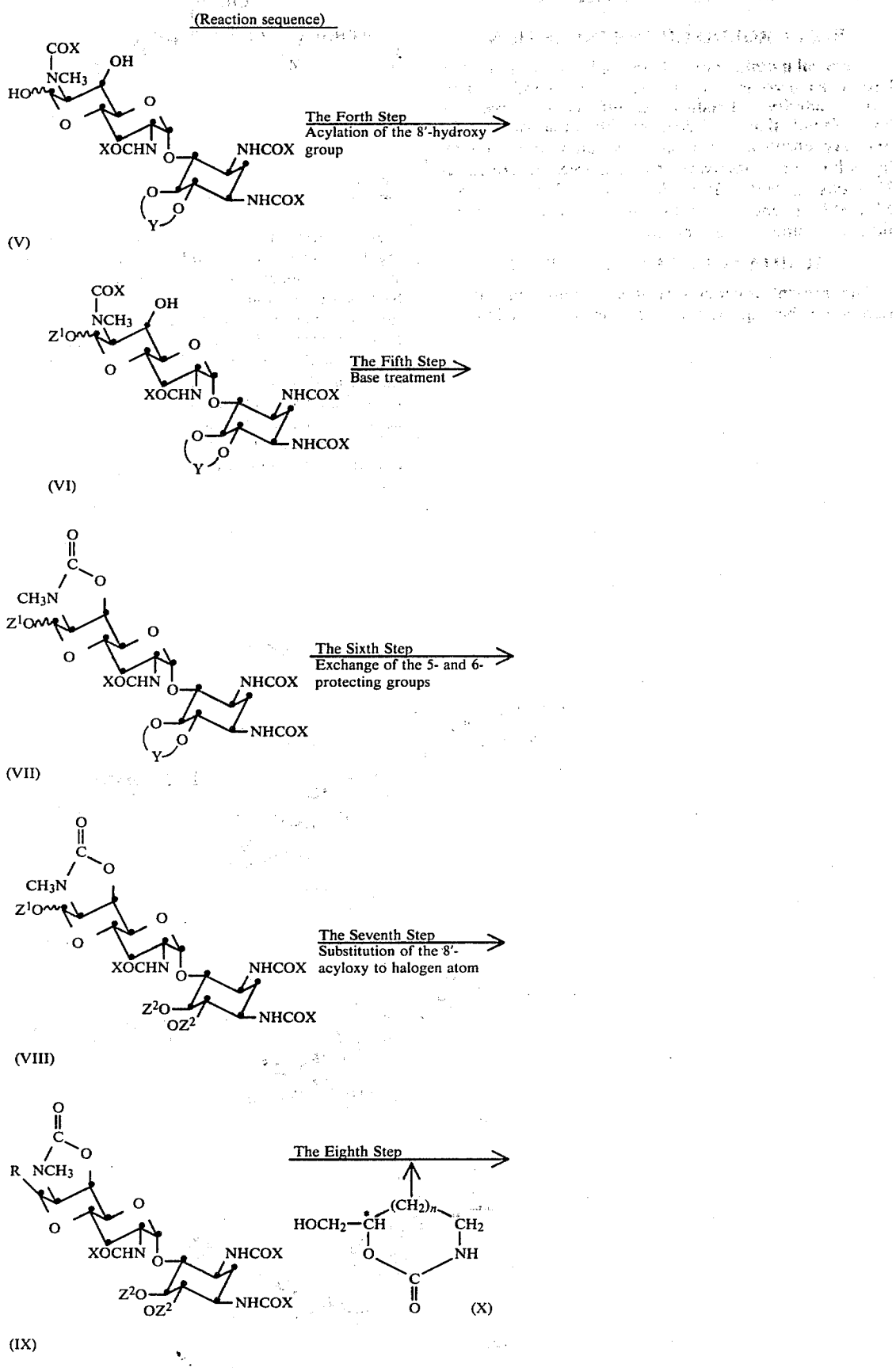

-continued
(Reaction sequence)

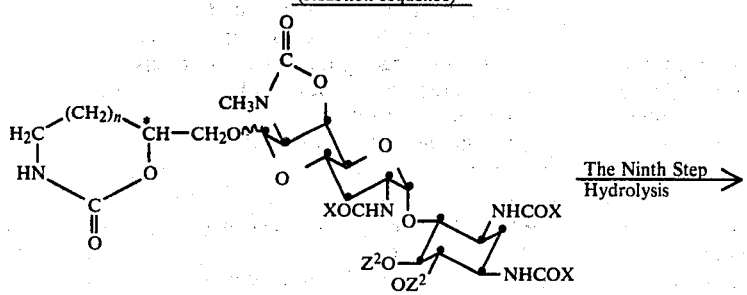

(XI)

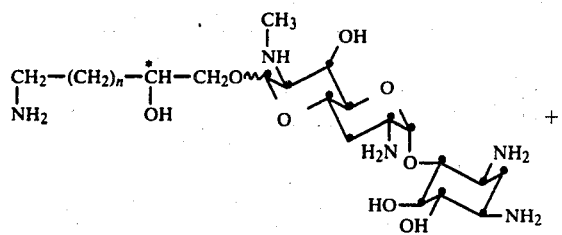

(I)

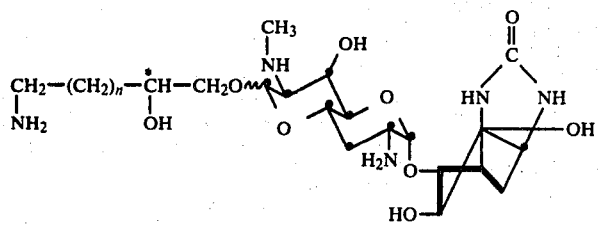

(XII)

(wherein,
COX is amino protecting group;
Y is cyclic hydroxy protecting group;
$Z^1$ is acyl group;
$Z^2$ is hydroxy protecting group;
R is halogen;
n and wave line have the same meaning as mentioned above)

(The First Step)

This step comprises hydrolysis of Apramycin, and may be conducted accordingly to the method which has been described in Journal of Organic Chemistry 41, 2087 (1976). In order to raise the yield, isolation and purification may be achieved with ion exchange resins.

(The Second Step)

This step comprises protection of the 1-, 3-, 2'- and 7'-amino groups of aprosamine. As a protecting group to be introduced, such groups that can readily be eliminated are preferably employed. For example, benzyloxycarbonyl in which the benzene ring may be substituted, formyl, t-butyloxycarbonyl, t-amyloxycarbonyl, methoxycarbonyl, ethoxycarbonyl, p-toluenesulfonyl, phthaloyl, m-nitrophenylthio and triphenylmethylthio are mentioned and particularly benzyloxycarbonyl is preferred.

The introduction of protecting groups is effected in the known method, for example, if the protecting group is benzyloxycarbonyl, more than 4 equivalent amount of carbobenzoxy chloride may be employed.

(The Third Step)

This step comprises protection of the 5- and 6-hydroxy groups. As a protecting group, such groups that can link the 5- and 6- hydroxy groups to form a ring are preferred. For example, cyclohexanone dialkylketal and dialkoxy propane, etc. are employed as a protecting agent and particularly cyclohexanone dimethylketal is preferred. The protecting agent may be employed in an equivalent amount or excess amount and preferably in 1-8 equivalent amount.

This step is a conventional method in a field of sugar chemistry, and may be conducted in a suitable inert solvent (benzene, toluene, xylene, etc.) in the presence of a catalytic amount of an acid (formic acid, acetic acid, p-toluenesulfonic acid).

(The Forth Step)

This step comprises acylation of the 8'-hydroxy group. As an acyl group to be introduced, formyl and acetyl are preferred and may be used in a form of the corresponding carboxylic anhydride and carboxylic acid halide (for example, carboxylic acid chloride, carboxylic acid bromide), etc. at room temperature or under heating. For example, if acetyl group is introduced, acetic anhydride may be employed in an equivalent amount or excess amount, and preferably 1-3 equivalent amount.

The acylating agents in this step also reacts with the 6'-hydroxy group to yield 6' 8' diprotected derivative as by-product. In such a case only 8' protected derivative may be separated by conventional methods like chromatography.

(The Fifth Step)

This step comprises intramolecular condensation between the 6'-hydroxy group and the 7'-amino protecting group and may be conducted in a suitable solvent (for example, hexane, diethyl ether, tetrahydrofuran, dimethylformamide, toluene) in the presence of a base. As a base employed, alkali metal hydride (lithium hydride, sodium hydride, potassium hydride, etc.), alkali metal hydroxide (sodium hydroxide, potassium hydroxide, etc.) and alkali metal alcoholate (sodium ethylate, potassium ethylate, etc.) can be employed, and alkali metal hydride, particularly sodium hydride is preferred.

(The Sixth Step)

This step comprises elimination of a cyclic hydroxy protecting group at the 5 and 6 positions which has been introduced at the third step and subsequent introduction of a hydroxy protecting group respectively into the hydroxy group at the 5 and 6 positions.

Elimination is achieved by hydrolysis with an acid. For example, inorganic acids (hydrochloric acid, sulfuric acid, phosphoric acid, etc.) and organic acids (formic acid, acetic acid, etc.) may preferably be employed according to the kind of protecting groups. This reaction is conducted at room temperature, and may be promoted under heating.

The subsequent introduction of protecting groups may be effected in the same manner as in the forth step, and the same protecting agents as disclosed in the forth step may also be used. In this reaction, more than 2 equivalent amount of the protecting agent may be employed.

(The Seventh Step)

This step comprises substitution of the 8'-acyloxy with halogen atom and can be achieved by a conventional method. As a halogenating agent, hydrogen halide, phosphorus halide, bromine or iodine with phosphorus, thionyl chloride and sulfuryl chloride are mentioned, and hydrogen halide gas particularly hydrogen chloride gas may preferably be introduced into the reaction mixture under cooling.

(The Eighth Step)

This step comprises condensation between the compounds (IX) and (X), and these two compounds may be reacted in the presence of a silver compound. As a silver compound, silver carbonate and/or silver perchlorate are preferred. The reaction may preferably be conducted in nitrogen atmosphere under shading at room temperature. And preferably, drying agent such as anhydrous calcium sulfate and anhydrous calcium carbonate may be added in the reaction medium.

The products (XI) consist of four stereoisomers due to the carbon atoms at the 8' position and indicated by * in the formula, and these can be separated by conventional separation procedures like chromatography.

(The Ninth Step)

This step comprises hydrolytic cleavage of the cyclic substituent introduced in the eighth step to chain form and hydrolytic elimination of the protecting groups introduced in the second and sixth steps. Hydrolysis is conducted in the presence of an alkali such as sodium hydroxide, potassium hydroxide and calcium hydroxide according to the known method.

The resulting products consist of stereoisomers, and if necessary, they can be separated by separation procedures like chromatography. The products may preferably be treated with an acid such as sulfuric acid to give the acid addition salt.

Aprosamine derivatives in the present invention and their non-toxic salts have superior antimicrobial activities and are more potent against some kinds of gram positive and negative bacteria than Apramycin. In the compounds wherein n is 0 and the wave line shows equatrial configuration in the general formula (I) and in Apramycin, minimum inhibitory concentrations (MIC; $\mu$g/ml) are shown as follows.

| Organism | Compound in the Present Invention | Apramycin |
| --- | --- | --- |
| Staphylococcus aureus APOI AAD(4') | 3.13 | 6.25 |
| Staphylococcus aureus FDA 209PJC-1 | 0.78 | 1.56 |
| Staphylococcus aureus S-25 | 0.78 | 1.56 |
| Staphylococcus aureus No. 74 | 1.56 | 3.13 |
| Staphylococcus epidermidis ATCC-14990 | 0.2 | 0.39 |
| Staphylococcus epidermidis EP-18 | 0.39 | 0.78 |
| Staphylococcus epidermidis TB-172 | 0.2 | 0.39 |
| Klebsiella pneumoniae Kl-159 | 25 | 50 |
| Psuedomonas aeruginosa TB-766 | 25 | >100 |
| Serratia marcescens MA-23 | 3.13 | 6.25 |
| Serratia marcescens MA-81 | 3.13 | 6.25 |
| Enterobacter aerogenes AE-16 | 3.13 | 6.25 |
| Enterobacter aerogenes AE-27 | 3.13 | 6.25 |
| Proteus rettgeri Ret-48 | 12.5 | 25 |
| Proteus rettgeri Ret-55 | 25 | 50 |
| Proteus morganii Morg-74 | 3.13 | 6.25 |
| Proteus morganii Morg-96 | 50 | >100 |
| Proteus vulgaris ATCC-6390 | 1.56 | 3.13 |

As shown in the above table, the compounds (I) in the present invention have potent antimicrobial activities against gram positive and gram negative bacteria, and so they are useful as drugs or animal drugs and are used in treatment or prevention of various infectious diseases caused by the above organisms. Moreover the compounds (I) in the present invention can be added to perishable foods as germicide and applied to bacteria intruding places and implements as disinfectant.

The compounds (I) in the present invention can be administered to human and other animals orally or parenterally. Particularly pharmacologically acceptable salts (for example, sulfate) can be administered as intravenous, intramuscular or subcutaneous injection in the form of aqueous solutions. The compounds (I) can be kept in ampoules in the form of solutions and may preferably be preserved in ampoules or vials in the form of crystals, powder, subtle crystals or lyophilizate and dissolved in water immediately before use. Stabilizer may be added.

Moreover the compounds (I) may be administered together with pharmaceutical components such as diluent (for example, starch, sucrose, lactose, calcium carbonate, kaolin) bulking (for example, lactose, starch, calcium carbonate, calcium phosphate, kaolin, bentonite, talc), lubricant (for example, stearic acid, paraffin, boric acid, silica, sodium benzoate, polyethylene glycol) in the form of powders, tablets, granules, capsules, troches, dry syrups, suppositories, suspensions, emulsions, inhalants, instillations, powders for local application or ointments. When the compounds (I) are applied in treatment of sensitive infectious diseases of human and animal, they are generally administered at 0.01–5 g (injection), preferably 0.02–0.2 g, 0.01–10 g (oral administration), preferably 0.05–0.5 g, or 0.01–10 g (local administration), preferably 0.05–0.5 g a day per 1 kg body weight every 3–12 hours. The dosage, however, is increased or decreased according to sensitivity of pathogenic bacteria, frequency of administration or status of the patient.

The following examples will demonstrate the present invention more in detail.

EXAMPLE

3-Amino-2-hydroxypropyl β-aprosaminide (a) Aprosamine (III)

Apramycin (II) trihydrate (11.880 g, 20 m mol) is dissolved in 4 N hydrochloric acid (500 ml), and stirred under heating at 95° C. for 5.5 hours. Active carbon (20 g) is added to the reaction mixture to decolor, filtrated, and concentrated under reduced pressure. Water (100 ml) is added to the residue and further concentrated under reduced pressure, and then this procedure is repeated one more time to give pale yellow foamy material (18.28 g). The resulting material is dissolved in water (100 ml) and adsorbed on an ion exchange resin Dowex 50 W×2 (H+) (240 ml) over a period of 36 minutes. The column is washed with water (300 ml) followed by elution with 5% hydrochloric acid to give 8 fractions and then with 10% hydrochloric acid after the 9th fraction successively (1 fraction: 100 ml). The fractions 3–5 are combined and evaporated under reduced pressure. The resulting residue is dissolved in water (20 ml), decolored with active carbon (1 g), and then evaporated to dryness under reduced pressure to give 4-amino-4-deoxy-D-glucopyranose hydrochloride (4.077 g) in 85.8% yield.

The fractions 13–24 are combined and concentrated under reduced pressure. Water is added to the resulting syrupy residue and concentrated under reduced pressure again. The residue is dissolved in water (10 ml) and acetone (200 ml) is added thereto and then the wall of the flask is rubbed with a glass bar. The supernatant is removed by decantation and the resulting oily residue is dissolved in water (3 ml) again. Acetone (150 ml) is added thereto and the wall of the flask is rubbed with a glass bar. The resulting powder is collected by filtration, washed with acetone, dissolved in water (150 ml), and decolorized with active carbon (3 g). The filtrate and washings are combined and evaporated to dryness under reduced pressure to give the tetrahydrochloride trihydrate of the titled compound (10.280 g) as white powder in 88.8% yield.

$[\alpha]_D^{22.0} + 53.0° \pm 0.9°$ C. (c=1.075, $H_2O$).

Elementary analysis: Calcd. (for $C_{15}H_{30}N_4O_7 \cdot 4HCl \cdot 3H_2O$) (%): C,31.15; H,6.97; Cl,24.52; N,9.69. Found (%): C,31.36; H,6.95; Cl,24.72; N,9.82.

NMR: $\delta_{ppm}^{D_2O}$ 6.40(d,$H_1$,J=4 Hz), 6.10(d,J=4 Hz), 5.80(d,J=9 Hz), 3.45(s).

(b) 1,3,2′,7′-Tetra-N-benzyloxycarbonylaprosamine
(IV:COX=COOCH$_2$Ph)

The product obtained in (a) (2.312 g, 4 mmol) is dissolved in water (20 ml), and sodium carbonate (1.90 g, 17.9 mmol) and acetone (20 ml) are added thereto, and then carbobenzoxy chloride (2.56 ml, 17.8 mmol, 1.12 equivalent) is added under cooling and stirred. After ten minutes the mixture is warmed up to room temperature, stirred for 3 hours, and the reaction mixture is extracted with ethyl acetate. The organic layer is washed with water, dried on sodium sulfate and concentrated under reduced pressure, and then ether is added thereto. The resulting precipitate is collected by filtration, dissolved in methanol, and ether is added to yield precipitate again. The precipitate is dried on phosphorus pentoxide under reduced pressure to give the titled compound (3.477 g) in 94.0% yield. A part of it is dissolved in chloroform-ethanol and hexane is added for crystallization to give the titled compound as pure fine prisms.

mp. 233°–234.5° C.

$[\alpha]_D^{22.0} + 48.8° \pm 0.9°$ (c=1.005, DMF).

IR: $\nu_{max}^{Nujol}$ 3570, 3366, 1692, 1531 cm$^{-1}$.

Elementary analysis: Calcd. (for $C_{47}H_{54}N_4O_{15} \cdot 0.5H_2O$) (%): C,61.10; H,6.00; N,6.06. Found (%): C,61.05; H,5.94; N,6.09.

(c)
1,3,2′,7′-Tetra-N-benzyloxycarbonyl-5,6-O-cyclohexylideneaprosamine

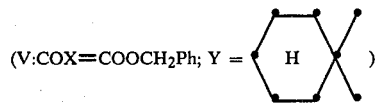

(V:COX=COOCH$_2$Ph; Y = )

The product obtained in (b) (2.823 g, 3.09 mmol) is dissolved in dimethylformamide (110 ml), and cyclohexanone dimethylketal (3.03 ml, 20.43 mmol; 6.6 equivalent) and p-toluenesulfonic acid (360 mg) are added and then the mixture is stirred under heating at an inner temperature of 50° C. under reduced pressure of 20 mmHg for 7.5 hours. The reaction mixture is cooled to room temperature and after addition of triethylamine (1 ml) poured into ice water (400 ml). The precipitate is collected by filtration, washed with water, dissolved in chloroform, dried on sodium sulfate, and evaporated under reduced pressure. The resulting residue (4 g) is chromatographed on a column [Adsorbent: Kiesel gel 60 (Merck Co.) 110 g; Eluent: benzene-ethyl acetate (3:1–1:1)], and the eluate is concentrated under reduced pressure to give the titled compound (2.575 g) in 84% yield. A part of it is crystallized from chloroform-ether to give subtle fine prisms as pure specimen.

mp. 142°–150° C.

$[\alpha]_D^{22.0} + 33.0° \pm 0.7°$ (c=1.022, CHCl$_3$).

IR: $\nu_{max}^{Nujol}$ 3430, 3375, 3340, 1720, 1698, 1665, 1545, 1523 cm$^{-1}$.

Elementary analysis: Calcd. (for $C_{53}H_{62}N_4O_{15} \cdot 1.5H_2O$) (%): C,62.28; H,6.41; N,5.48. Found (%): C,62.29; H,6.32; N,5.37.

(d)
8′-O-Acetyl-1,3,2′,7′-tetra-N-benzyloxycarbonyl-5,6-O-cyclohexylideneaprosamine

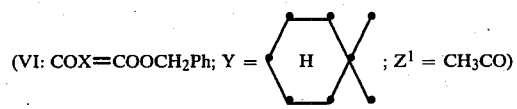

(VI: COX=COOCH$_2$Ph; Y = ; $Z^1$ = CH$_3$CO)

The product obtained in (c) (23.50 g, 23.6 mmol) is dissolved in pyridine (450 ml), and pyridine (20 ml) is removed under reduced pressure. Acetic anhydride (4.7 ml, 50 mmol, 2.1 equivalent) is added thereto under ice cooling and the mixture is kept at 0° C. for 3 days followed by concentration under reduced pressure. The residue is dissolved in ether (150 ml), and the seed crystals of the titled compound are added and then kept at room temperature. The resulting crystals (19.6 g) are further recrystallized from chloroformethanol to give the titled compound (15.964 g) as prisms in 65.3% yield. A part of it is further recrystallized from methanol.

mp. 210°–212° C.
$[\alpha]_D^{23.0} + 32.0° \pm 0.7°$ (c=1.012, CHCl$_3$).
IR: $\nu_{max}^{Nujol}$ 3585, 3360, 1755, 1697, 1525 cm$^{-1}$.

Elementary analysis: Calcd. (for C$_{55}$H$_{64}$N$_4$O$_{16}$) (%): C,63.64; H,6.22; N,5.40. Found (%): C,63.37; H,6.22; N,5.40.

The mother liquor (6 g) obtained in the first crystallization and that (3.6 g) obtained after recrystallization are combined and chromatographed on a column [Adsorbent: Kiesel gel 60 (Merck Co.) 190 g; Eluent: benzene-ethyl acetate (8:2)] to give 6′,8′-di-O-acetyl-1,3,2′,7′-tetra-N-benzyloxycarbonyl-5,6-O-cyclohexylideneaprosamine (2.589 g) in 10.1% yield as by-product.

$[\alpha]_D^{23.5} + 37.2° \pm 0.7°$ (c=1.047, CHCl$_3$).
IR: $\nu_{max}^{CHCl_3}$ 3440, 1752, 1720, 1511 cm$^{-1}$.

Elementary analysis: Calcd. (for C$_{58}$H$_{66}$N$_4$O$_{17}$) (%): C,63.44; H,6.16; N,5.19. Found (%): C,63.26; H,6.11; N,5.15.

In addition, elution with benzene-ethyl acetate (7.5:2.5) gives an additional amount of the titled compound (5.0 g). This is recrystallized from chloroform-ether to give prisms (3.602 g) with mp. 203°–206° C. in 14.8% yield. Total yield of the titled compound: 19.566 g (80.1%)

(e)
8′-O-Acetyl-1,3,2′-tri-N-benzyloxycarbonyl-7′-N-6′-O-carbonyl-5,6-O-cyclohexylideneaprosamine

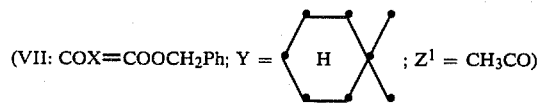

(VII: COX=COOCH$_2$Ph; Y = ⟨cyclohexylidene⟩ ; Z$^1$ = CH$_3$CO)

The product obtained in (d) (25.780 g, 24.86 mmol) is dissolved in dimethylformamide (200 ml) and tetrahydrofuran (800 ml) and cooled with ice under stirring in nitrogen atmosphere, and then 50% sodium hydride (1.40 g, 29.16 mmol, 1.17 equivalent) is added without washing. After 50 minutes acetic acid (1.8 ml, 30 mmol) is added, and the solvent is removed under reduced pressure. Pyridine (200 ml) and acetic anhydride (100 ml) are added to the residue, kept at room temperature for 2 hours and concentrated under reduced pressure, and then the residue is poured into ice water. The precipitate is collected by filtration, washed with water, dissolved in chloroform, dried on sodium sulfate and concentrated under reduced pressure. To the concentrated solution is added n-hexane, and the resulting precipitate is collected by filtration to give the titled compound (24 g) as crude product. A part of it is purified by column chromatography [Adsorbent: Kiesel gel 60 (Merck Co.); Eluent: chloroform containing 1% methanol].

$[\alpha]_D^{23} + 32.7° \pm 0.7°$ (c=0.952, CHCl$_3$).
IR: $\nu_{max}^{CHCl_3}$ 3440, 1762, 1720, 1512 cm$^{-1}$.

Elementary analysis: Calcd. (for C$_{48}$H$_{56}$N$_4$O$_{15}$) (%): C, 62.06; H, 6.08; N, 6.03. Found (%): C, 61.84; H, 6.07; N, 5.94.

(f)
5,6,8′-Tri-O-acetyl-1,3,2′-tri-N-benzyloxycarbonyl-7′-N-6′-O-carbonylaprosamine (VIII: COX=COOCH$_2$Ph; Z$^1$=Z$^2$=CH$_3$CO)

The crude product (23.9 g) obtained in (e) is dissolved in acetic acid (200 ml) and water (50 ml), stirred under heating at 60° C. for 1 hour and then cooled to 3° C. The resulting precipitate is collected by filtration, washed with acetone and ether successively and dissolved in pyridine (200 ml) and acetic anhydride (100 ml). The resulting solution is heated at 60° C. for 8 hours, allowed to stand overnight at room temperature and poured into ice water. The precipitate is collected by filtration, washed with water, dissolved in chloroform, washed with 10% hydrochloric acid, water, 5% sodium hydrogencarbonate and water successively, dried on sodium sulfate, and evaporated under reduced pressure. The resulting residue is chromatographed [Adsorbent: Kiesel gel 60 (Merck Co.); Eluent: chloroform and chloroform-methanol (98:2)]. The eluate is evaporated to dryness under reduced pressure and recrystallized from chloroform-ethanol to give the titled compound.

The first crop: 18.113 g (Yield: 78.1%)
mp. 261.5°–263° C.
The second crop: 1.009 g (Yield: 4.8%)
mp. 262°–263° C.
Total yield 19.122 g (82.9%)

A part of the first cropped crystals are recrystallized from chloroform-hexane again to give the titled compound as pure specimen.

mp. 263°–265° C.
$[\alpha]_D^{25} + 34.5° \pm 0.7°$ (c=1.041, CHCl$_3$).
IR: $\nu_{max}^{Nujol}$ 3360, 1758, 1744, 1697, 1531 cm$^{-1}$.

Elementary analysis: Calcd. (for C$_{46}$H$_{52}$N$_4$O$_{17}$) (%): C, 59.22; H, 5.62; N, 6.06. Found (%): C, 59.24; H, 5.55; N, 6.00.

(g)
5,6-Di-O-acetyl-1,3,2′-tri-N-benzyloxycarbonyl-7′-N-6′-O-carbonylaprosaminyl chloride (IX: COX=COOCH$_2$Ph; Z$^2$=CH$_3$CO; R=Cl)

The product obtained in (f) (3.000 g, 3.22 mmol): is dissolved in dry chloroform (105 ml) and about 10 ml of the solvent is removed by azeotropic distillation at atmospheric pressure. Acetic anhydride (0.38 ml) is added under cooling, and hydrogen chloride gas is introduced therein for 3.5 hours and then the solvent is evaporated under reduced pressure at room temperature to give the titled compound (3.153 g). This is recrystallized twice from a mixture of chloroform and acetonitrile and successively once from acetonitrile to give the titled compound (2.047 g) as fine needles in 70.0% yield.

mp. 257°–257.5° C. (decomposition).
$[\alpha]_D^{26.5} - 35.1° \pm 0.8°$ (c=1.001, DMF).

Elementary analysis: Calcd. (for C$_{44}$H$_{49}$ClN$_4$O$_{15}$) (%): C, 58.11; H, 5.43; Cl, 3.90; N, 6.16. Found (%): C, 58.16; H, 5.37; Cl, 4.12; N, 6.16.

(h) (2-Oxazolidin-5-yl)methyl 5,6-di-O-acetyl-1,3,2′-tri-N-benzyloxycarbonyl-7′-N-6′-O-carbonyl-β-aprosaminide (XI: COX=COOCH$_2$Ph; Z$^2$=CH$_3$CO; n=0)

The product obtained in (g) (2.000 g, 2.2 mmol) and 5-hydroxymethyl-2-oxazolidinone (X) (produced by the method disclosed in Jap. Unexam. Pat. Pub. No. 51-16661) (618 mg, 5.28 mmol, 2.4 equivalent) are dissolved in dry chloroform (600 ml) and concentrated at atmospheric pressure to about 400 ml. Then, silver carbonate (1.280 g, 4.64 mmol, 1.14 equivalent), Drierite (dried under reduced pressure at 110° C. on phosphorus pentoxide [W. A. Hammond Drierite Co., Xenia, Ohio, U.S.A.] (8.780 g) and silver perchlorate (130 mg, 0.627 mmol) are added thereto successively in nitrogen atmosphere at room temperature, and the mixture is stirred under shading at room temperature. After 1.5 hours inorganic material is removed by filtration and washed with chloroform. The filtrate and washings are combined, washed with 5% sodium hydrogencarbonate solution and water, dried on sodium sulfate and evaporated under reduced pressure. The residue (2.23 g) is applied to liquid chromatography using two prepack columns (size B; Merck Co.) arranged in series and eluted with acetonitrile-chloroform (1:1) to the fraction 150 and with acetonitrile after the fraction 151 (1 fraction: 20 ml, flow rate: 10 ml/min.). The fractions 54–130 are combined, and the solvent is removed under reduced pressure and then the resulting residue (1.349 g) is eluted on the same column as mentioned above with chloroform-methanol (19:1) (1 fraction: 15 ml, flow rate: 15 ml/min.). The fractions 27–42 are combined, and the solvent is removed under reduced pressure and then the resulting residue (1.243 g) is precipitated with chloroform-hexane to give a mixture of stereoisomers of the titled compound (in the general formula (XI) the wave line indicates equatrial configuration (1.241 g) as powder in 56.0% yield.

$[\alpha]_D^{24.5} +21.8° \pm 0.6°$ (c=1.060, CHCl$_3$).

IR: $\nu_{max}^{CHCl_3}$ 3480, 3430, 3303, 1755, 1717, 1509 cm$^{-1}$.

Elementary analysis: Calcd. (for C$_{48}$H$_{55}$N$_5$O$_{18}$.H$_2$O) (%): C, 57.19; H, 5.70; N, 6.95. Found (%): C, 57.41; H, 5.58; N, 6.75.

NMR: $\delta_{ppm}^{CDCl-CD3OD(2:1)}$ 7.38(s), 5.10(s), 2.74(s), 1.86(s), 1.77(s).

The fractions 152–161 in the first chromatography are combined, and the solvent is removed to give one (a) of the stereoisomers of the titled compound (in the general formula (XI) the wave line indicates axial configuration) (100 mg).

The fractions 162–210 are combined, and the solvent is removed by distillation under reduced pressure to give a mixture of the stereoisomers (a+b) of the titled compound (in the general formula (XI) the wave line indicates axial configuration (584 mg). The mixture is chromatographed on the same column as mentioned above and eluted with chloroform-methanol (19:1) (1 fraction: 20 ml, flow rate: 8 ml/min.). The fractions 10–14 are combined, and the solvent is removed by distillation under reduced pressure. The resulting residue (240 mg) and the above stereoisomer (a) (100 mg) are combined and precipitated with chloroform-hexane to give the stereoisomer (a) of the titled compound (in the general formula (XI) the wave line indicates axial configuration) (323 mg) in 14.6% yield.

The fractions 16–27 are combined, and the solvent is removed by distillation under reduced pressure and then the resulting residue (328 mg) is precipitated with chloroform-hexane to give the stereoisomer (b) of the titled compound (the wave line indicates axial configuration) (317 mg) in 14.5% yield.

Stereoisomer (a)

$[\alpha]_D^{24.5} -21.8° \pm 0.6°$ (c=1.071, CHCl$_3$).

IR: $\nu_{max}^{CHCl_3}$ 3425, 3290, 1756, 1720, 1505 cm$^{-1}$.

Elementary analysis: Calcd. (for C$_{48}$H$_{55}$N$_5$O$_{18}$.H$_2$O) (%): C, 57.19; H, 5.70; N, 6.95. Found (%): C, 56.92; H, 5.42; N, 6.82.

NMR: $\delta_{ppm}^{CDCl_3-CD3OD(2:1)}$ 7.40(s), 5.07(s), 2.55(s), 1.83(s), 1.70(s).

Stereoisomer (b)

$[\alpha]_D^{24.5} +4.0° \pm 0.4°$ (c=0.986, CHCl$_3$).

IR: $\nu_{max}^{CHCl_3}$ 3430, 3290, 1758, 1720, 1513 cm$^{-1}$.

Elementary analysis: Calcd. (for C$_{48}$H$_{55}$N$_5$O$_{18}$.H$_2$O) (%) C, 57.19; H, 5.70; N, 6.95. Found (%): C, 56.92; H, 5.38; N, 6.85.

NMR: $\delta_{ppm}^{CDCl_3-CD3OD(2:1)}$ 7.38(s), 5.10(s), 2.60(s), 1.86(s), 1.83(s).

(i) 3-Amino-2-hydroxypropyl β-aprosaminide (I:n=0)

A mixture of the stereoisomers (in the general formula (XI) the wave line indicates equatrial configuration) (600 mg, 0.595 mmol) obtained in (h) is dissolved in dioxane (7.2 ml), and then water (7.2 ml) and 2 N sodium hydroxide solution (17.8 ml, 35.6 mmol, 59.8 equivalent) are added and refluxed in nitrogen atmosphere for 3 hours. The reaction mixture is cooled at room temperature and adjusted at pH 7 with 10% hydrochloric acid (12 ml). The resulting solution is adsorbed on an ion exchange resin Amberlite CG-50 (NH$_4^+$) (144 ml), and the column is washed with water (720 ml) and eluted with water (1 liter) and 0.3 N ammonium hydroxide (1 liter) by the gradient method to the fraction 150 and with 1 N ammonium hydroxide after the fraction 151 (1 fraction: 10 ml). All fractions after the fraction 151 are concentrated under reduced pressure, and the resulting residue (188 mg) is adsorbed on CG-50 (NH$_4^+$) (132 ml) again, and the column is washed with water (660 ml) and eluted with water (1 liter) and 1 N ammonium hydroxide (1 liter) by the gradient method (1 fraction: 13 ml).

The fractions 74–85 are combined, concentrated under reduced pressure, and the resulting residue (180 mg) is adsorbed on CM-Sephadex C-25 (NH$_4^+$) (132 ml) and then column is washed with water (660 ml) and eluted with water (1 liter) and 0.5 N ammonium hydroxide (1 liter) by the gradient method (1 fraction: 14 ml).

The fractions 82–93 are combined and concentrated under reduced pressure. The resulting residue (162 mg) is adjusted at pH 4.50 with 0.1 N sulfuric acid (15 ml), concentrated under reduced pressure to about 1–2 ml, and ethanol is added thereto. The resulting precipitate is collected by filtration, washed with ethanol, dissolved in water, and treated with active carbon (23 mg). After 30 minutes the mixture is filtered through a glass filter (Millipore Corp.), washed with water, and the filtrate and washings are combined and then lyophilized. The resulting residue is kept in a desiccator containing sodium bromide (200 g) and water (100 ml) until the weight becomes constant to give the titled compound as sulfate (251 mg) in 49.6% yield.

$[\alpha]_D^{23} +66.8° \pm 1.0°$ (c=1.066, H$_2$O).

Elementary analysis: Calcd. (for C$_{18}$H$_{37}$N$_5$O$_8$.2.5H$_2$SO$_4$.8.5H$_2$O) (%): C, 25.44; H, 7.00; N, 8.24; S, 9.43. Found (%): C, 25.35; H, 6.93; N, 8.33; S, 9.58.

NMR: $\delta_{ppm}^{D2O}$ 6.33(d,J=4 Hz), 5.57(d,J=9 Hz), 3.38(s).

The fractions 120–150 in the first chromatography are combined, concentrated under reduced pressure, and the resulting residue (98 mg) is adsorbed on CM-Sephadex C-25 ($NH_4^+$) (60 ml). The column is washed with water (300 ml) and eluted with water (1 liter) and 0.15 N ammonium hydroxide (1 liter) by the gradient method (1 fraction: 11 ml). The fractions 82–97 are combined, concentrated under reduced pressure, and the resulting residue (90 mg) is dissolved in water (1 ml) and adjusted at pH 4.50 with 0.1 N sulfuric acid (5 ml). The solution is concentrated under reduced pressure to about 1–2 ml and ethanol is added thereto. The resulting precipitate is collected by filtration, washed with ethanol, dissolved in water, and treated with active carbon (10 mg). After 30 minutes the mixture is filtrated through a glass filter (Millipore Corp.), and the filtrate and washings are combined and then lyophilized. The resulting residue is kept in a desiccator containing sodium bromide (200 g) and water (100 ml) until the weight becomes constant to give 3-amino-2-hydroxypropyl 1,3-N,N-carbonyl-β-aprosaminide (XII: n=0) sulfate (120 mg) as by-product in 26.8% yield.

$[\alpha]_D^{24.0} + 93.1° \pm 1.3°$ (c=1.001, $H_2O$).

Elementary analysis: Calcd. (for $C_{19}H_{35}N_5O_9 \cdot 1.5H_2SO_4 \cdot 7H_2O$) (%): C, 30.40; H, 6.98; N, 9.33; S, 6.41. Found (%): C, 30.53; H, 6.97; N, 9.41; S, 6.50.

NMR: $\delta_{ppm}^{D_3O}$ 5.93 (d, J=4 Hz), 5.60 (d, J=9 Hz), 3.40 (s).

What is claimed is:

1. An aprosamine derivative having the following general formula and its pharmaceutically acceptable acid addition salts:

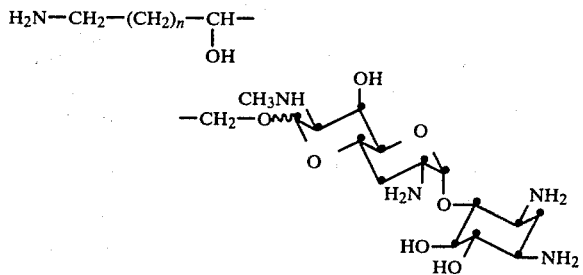

(wherein n is 0 or 1; the wave line indicates axial or equatorial configuration).

2. An aprosamine derivative claimed in claim 1, wherein n is 0 and the wave line indicates equatorial configuration.

* * * * *

UNITED STATES PATENT AND TRADEMARK OFFICE
CERTIFICATE OF CORRECTION

PATENT NO. : 4,362,866          Page 1 of 5
DATED      : December 7, 1982
INVENTOR(S): Kikuo IGARASHI and Tsunetoshi HONMA It is certified that error appears in the above—identified patent and that said Letters Patent is hereby corrected as shown below:

IN THE ABSTRACT:
   line 1 thereof, delete "the".

Column 2, line 2 of the description of formula (I), change "a wave" to --wavy--;
   immediately after formula (I) and its description, insert the following heading:
   --DETAILED DESCRIPTION OF THE INVENTION--;
   line 2 of the first full paragraph of column 2, delete "also";
   line 12 thereof, change "accordingly" to --according--;
   directly above formula (II), delete "(Reaction sequence)";
   Column 3, directly above formula (V), delete "(Reaction sequence)";
   in the description of formula (V), change "Forth" to --Fourth--;
   Column 5, line 38, after "is" insert --an--;
            line 39, after "is" insert --a--;
            line 40, after "is" insert --an--;
            line 41, after "is" insert --a--;
            line 43, change "wave" to --the wavy--;
            line 48, change "accordingly" to --according--;
            line 62, after "mentioned" insert --,--;
            line 64, change "in" to --by--;
            line 65, change "the known" to --a known--;
            line 66, after "4" insert --times the--;
   Column 6, line 44, after "agent" insert --,--;
            line 46, change "and" to --,--; after "in" insert --an amount of--;

UNITED STATES PATENT AND TRADEMARK OFFICE
CERTIFICATE OF CORRECTION

PATENT NO. : 4,362,866
DATED : December 7, 1982
INVENTOR(S) : Kikuo IGARASHI and Tsunetoshi HONMA It is certified that error appears in the above—identified patent and that said Letters Patent is hereby corrected as shown below:

Column 6, line 47, change "equivalent amount" to --equivalents--;
line 48, change "in a" to --in the--;
between lines 52 and 55, change "Forth" to --Fourth--;
line 57, change "a" to --the--;
line 58, change "and" to --or--;
line 61, after "if" insert --the--;
line 63, delete "and";
line 64, change "equivalent amount" to --equivalents--;
line 65, change "agents" to --agent--;
line 66, after "yield" insert --the--; change "6´8´ diprotected" to --6´,8´-diprotected--;
line 67, after "only" insert --the--;
Column 7, line 10, change "a base employed," to --the base,--;
line 20, after "step" insert --,--;
line 31, change "forth" to --fourth--;
line 32, change "forth" to --fourth--;
line 34, change "equivalent amount" to --equivalents--;
line 43, after "gas" insert --,--;
line 53, after "in" insert --a--;
line 54, change "And preferably," to --Preferably, a--;
line 57, change "products (XI) consist" to --product (XI) consists--;
line 58, change "atoms" to --atom--; change "and" to --as--;
line 64, after "to" insert --the--;

UNITED STATES PATENT AND TRADEMARK OFFICE
CERTIFICATE OF CORRECTION

PATENT NO. : 4,362,866
DATED : December 7, 1982
INVENTOR(S) : Kikuo IGARASHI and Tsunetoshi HONMA It is certified that error appears in the above—identified patent and that said Letters Patent is hereby corrected as shown below:

Column 8, line 3, change "products consist" to --product consists--;
line 12, change "wave" to --wavy--;
line 13, change "equatrial" to --equatorial--;
line 4 below the table, delete "or animal drugs and are used";
line 8 thereof, after "bacteria" insert a hyphen(-);
line 24 thereof, after "bulking" insert --agent--;

Column 9, line 1, change "human" to --humans--;
line 2, change "mal," to --mals,--;
line 5, after "g" insert --,--;
line 19, change ", filtrated," to --it, and the mixture is filtered--;
line 21, change "and" to --which is then--;
line 39, change "and" to --which is then--;
line 51, change "titled" to --title--;
line 54, change "Elementary" to --Elemental--;

Column 10, line 8, change "titled" to --title--;
line 11, change "titled" to --title--;
line 15, change "Elementary" to --Elemental--;
line 44, change "titled" to --title--;
line 51, change "Elementary" to --Elemental--;

Column 11, line 3, delete "the";
line 4, change "titled" to --title--;
line 7, change "titled" to --title--;
line 12, change "Elementary" to --Elemental--;
line 25, change "Elementary" to --Elemental--;
line 29, change "titled" to --title--;
line 32, change "titled" to --title--;
line 60, change "titled" to --title--;

UNITED STATES PATENT AND TRADEMARK OFFICE
CERTIFICATE OF CORRECTION

PATENT NO. : 4,362,866

DATED : December 7, 1982

INVENTOR(S) : Kikuo IGARASHI and Tsunetoshi HONMA

It is certified that error appears in the above—identified patent and that said Letters Patent is hereby corrected as shown below:

Column 12, line 1, change "Elementary" to --Elemental--;
line 26, change "titled" to --title--;
line 32, change "cropped crystals are" to --crop of crystals is--;
line 33, change "titled" to --title--;
line 38, change "Elementary" to --Elemental--;
line 53, change "titled" to --title--;
line 55, change "titled" to --title--;
line 59, change "Elementary" to --Elemental--;
Column 13, line 30, change "titled" to --title--;
line 31, change "wave" to --wavy--; and change "equatrial" to --equatorial--;
line 36, change "Elementary" to --Elemental--;
line 43, change "titled" to --title--;
line 44, change "wave" to --wavy--;
line 48, change "titled" to --title--;
line 49, change "wave" to --wavy--;
line 50, after "configuration" insert --)--;
line 58, change "titled" to --title--;
line 59, change "wave" to --wavy--;
line 65, change "titled" to --title--; change "wave" to --wavy--;
Column 14, line 5, change "Elementary" to --Elemental--;
line 14, change "Elementary" to --Elemental--;
line 23, change "wave" to --wavy--; change "equatrial" to --equatorial--;
line 46, change "then" to --the--;
line 61, change "titled" to --title--;
line 64, change "Elementary" to --Elemental--;

UNITED STATES PATENT AND TRADEMARK OFFICE
CERTIFICATE OF CORRECTION

PATENT NO. : 4,362,866

DATED : December 7, 1982

INVENTOR(S) : Kikuo IGARASHI and Tsunetoshi HONMA

It is certified that error appears in the above—identified patent and that said Letters Patent is hereby corrected as shown below:

Column 15, line 15, change "filtrated" to --filtered--;
Column 16, line 1, change "Elementary" to --Elemental--.

IN THE CLAIMS:
Amend the claims as follows:
Claim 1, line 1, change "An aprosamine derivative" to --A compound--;
line 2, change "general formula and" to --formula or--;
line 3, change "salts" to --salt--;
line 1 below the formula, delete "("; change "the wave" to --and the wavy--;
line 2 below the formula, delete ")".
Claim 2, line 1, change "An aprosamine derivative" to --A compound--;
line 2, change "wave" to --wavy--.

Signed and Sealed this

Nineteenth Day of April 1983

[SEAL]

Attest:

GERALD J. MOSSINGHOFF

Attesting Officer    Commissioner of Patents and Trademarks